US00PP14934P2

(12) United States Plant Patent
Dekker

(10) Patent No.: US PP14,934 P2
(45) Date of Patent: Jun. 22, 2004

(54) CHRYSANTHEMUM PLANT NAMED 'GREENSPAN'

(50) Latin Name: *Chrysanthemum×morifolium*
Varietal Denomination: Greenspan

(75) Inventor: Nicolaas P. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 10/654,356

(22) Filed: Sep. 2, 2003

(51) Int. Cl.[7] ..... A01H 5/00
(52) U.S. Cl. ..... Plt./287
(58) Field of Search ..... Plt./287

*Primary Examiner*—Anne Marie Grunberg
(74) *Attorney, Agent, or Firm*—C. A. Whealy

(57) ABSTRACT

A new and distinct cultivar of Chrysanthemum plant named 'Greenspan', characterized by its decorative type inflorescences with white and green-colored ray florets; strong and upright flowering stems; freely flowering habit; early flowering response; and good postproduction longevity.

1 Drawing Sheet

Botanical classification/cultivar designation: *Chrysanthemum×morifolium* cultivar Greenspan.

BACKGROUND OF THE INVENTION

The present invention relates to a new and distinct cultivar of Chrysanthemum plant, botanically known as *Chrysanthemum×morifolium* and referred to by the name 'Greenspan'.

The new Chrysanthemum is the product of a planned breeding program conducted by the Inventor in Hensbroek, The Netherlands. The new Chrysanthemum originated from a cross-pollination made by the Inventor on Nov. 23, 1999, in Hensbroek, The Netherlands, of a proprietary selection of Chrysanthemum identified as code number 5003.26, not patented, as the female, or seed, parent with a proprietary Chrysanthemum selection identified as code number 97.174.03, not patented, as the male, or pollen, parent. The new Chrysanthemum was discovered and selected by the Inventor as a single plant within the progeny of the stated cross-pollination in a controlled environment in Hensbroek, The Netherlands.

Asexual reproduction of the new Chrysanthemum by terminal cuttings in Hensbroek, The Netherlands since April, 2000, has shown that the unique features of this new Chrysanthemum are stable and reproduced true to type in successive generations.

BRIEF SUMMARY OF THE INVENTION

The cultivar Greenspan has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Greenspan'. These characteristics in combination distinguish 'Greenspan' as a new and distinct cultivar:

1. Decorative type inflorescences with white and green-colored ray florets; typically grown as a spray type.
2. Strong and upright flowering stems.
3. Freely flowering habit.

4. Early flowering response.
5. Good postproduction longevity.

Compared to plants of the female parent selection, plants of the new Chrysanthemum grow faster, have smaller leaves, are more freely flowering, and have fewer ray florets per inflorescence. In addition, plants of the new Chrysanthemum and the female parent selection differ in ray floret coloration as plants of the female parent have yellow-colored ray florets.

Compared to plants of the male parent selection, plants of the new Chrysanthemum grow faster, have larger inflorescences, and differ in inflorescence form. In addition, plants of the new Chrysanthemum and the male parent selection differ in ray floret coloration as plants of the male parent have yellow green-colored ray florets.

Plants of the new Chrysanthemum can be compared to plants of the Chrysanthemum cultivar Leonardo, not patented. In side-by-side comparisons conducted in Hensbroek, The Netherlands, plants of the new Chrysanthemum differed from plants of the cultivar Leonardo in the following characteristics:

1. Plants of the new Chrysanthemum grew faster than plants of the cultivar Leonardo.
2. Plants of the new Chrysanthemum were more freely flowering than plants of the cultivar Leonardo.
3. Plants of the cultivar Leonardo had green-colored ray florets than plants of the new Chrysanthemum.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Greenspan'.

The photograph at the bottom of the sheet comprises a close-up view of typical leaves and inflorescences of 'Greenspan'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the spring in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5 to 22° C., night temperatures were about 18.5° C., and light levels were about five kilolux. Plants were pinched once and were about eleven weeks from planting when the photographs and the description were taken.

Botanical classification: *Chrysanthemum×morifolium* cultivar Greenspan.

Commercial classification: Decorative type Chrysanthemum typically grown as a spray-type cut flower.

Parentage:

*Female or seed parent.*—Proprietary selection of *Chrysanthemum×morifolium* identified as code number 5003.26, not patented.

*Male or pollen parent.*—Proprietary selection of *Chrysanthemum×morifolium* identified as code number 97.174.03, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine and freely branching; light brown in color.

Plant description:

*Appearance.*—Herbaceous decorative type cut Chrysanthemum; typically grown as a spray type; erect and strong flowering stems.

*Growth rate.*—Moderate; moderately vigorous.

*Flowering stem description.*—Length: About 90 to 100 cm. Diameter, at apex: About 6 mm. Strength: Strong. Aspect: Erect. Branching habit: Plants are typically grown as single stems, but if pinched, will develop 10 to 13 lateral stems. Color: 146C.

*Foliage description.*—Arrangement: Alternate. Length: About 8 to 11 cm. Width: About 4 to 7 cm. Apex: Acute. Base: Acute. Margin: Pinnately lobed. Texture: Rough; both surfaces pubescent. Petiole length: About 1 to 3 cm. Color: Developing and fully expanded foliage, upper surface: 137B. Developing and fully expanded foliage, lower surface: 137C. Venation, upper and lower surfaces: 147C. Petiole: 147C.

Inflorescence description:

*Appearance.*—Decorative type inflorescence form with elongated oblong-shaped ray florets. Inflorescences borne on terminals above foliage. Disk and ray florets develop acropetally on a capitulum. Not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 52 days later.

*Postproduction longevity.*—Inflorescences will maintain good substance and form for about two weeks after harvesting.

*Quantity of inflorescences per flowering stem.*—About 12 to 15 inflorescences per flowering stem.

*Inflorescence size.*—Diameter: About 3 to 4 cm. Depth (height): About 1.5 to 2.5 cm. Diameter of disc: About 7 mm.

*Inflorescence buds.*—Length: About 4 to 6 mm. Diameter: About 1 to 1.3 cm. Shape: Oblate. Color: 138B.

*Ray florets.*—Length, fully developed: About 1.6 to 2 cm. Width, fully developed: About 5 to 6 mm. Shape: Elongated oblong. Apex: Rounded. Base: Fused, short corolla tube. Margin: Entire. Texture: Smooth, glabrous. Number of ray florets per inflorescence: About 200. Color: When opening, upper and lower surfaces: 144A. Fully opened, upper and lower surfaces: Towards the base, 155A; towards the apex, 144B; color towards the apex becoming closer to 144C with development.

*Disc florets.*—Shape: Oblong, tubular. Length: About 6 mm. Width: About 1 to 2 mm. Number of disc florets per inflorescence: About 15. Color: Immature: 155C. Mature: Towards the base, 155C; towards the apex, 12A.

*Peduncles.*—Length, terminal peduncle: About 5.5 cm. Length, fourth peduncle: About 8 cm. Diameter: About 2 to 3 mm. Angle: About 45° from vertical. Texture: Pubescent. Color: 146B.

*Reproductive organs.*—Androecium: Present on disc florets only. Anther color: 151C. Pollen color: 23A. Gynoecium: Present on both ray and disc florets. Stigma length: About 1 mm. Stigma width: About 0.3 mm. Stigma color: Towards the apex, 151B; towards the base, 144C to 144D.

*Seed/fruit.*—Seed and fruit production has not been observed.

Disease/pest resistance: Resistance to known Chrysanthemum pathogens and pests has not been observed on plants of the new Chrysanthemum.

It is claimed:

1. A new and distinct cultivar of Chrysanthemum plant named 'Greenspan', as illustrated and described.

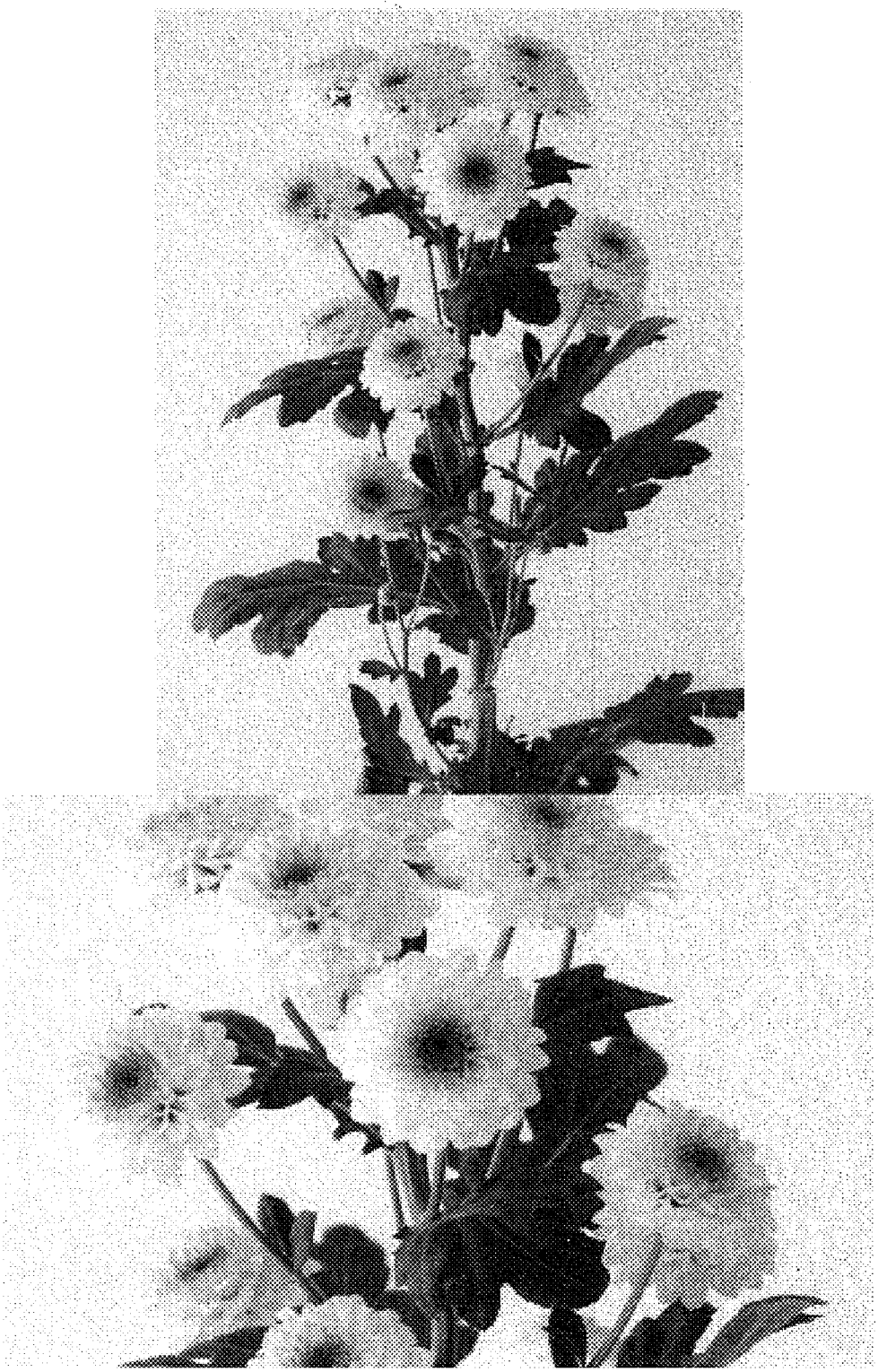

* * * * *